(12) United States Patent
Loubens

(10) Patent No.: US 10,260,135 B2
(45) Date of Patent: Apr. 16, 2019

(54) HYPERELASTIC NEEDLES

(71) Applicant: SOPRANE, Villeurbanne (FR)

(72) Inventor: Thierry Loubens, Lyons (FR)

(73) Assignee: SOPRANE, Villeurbanne (FR)

( * ) Notice: Subject to any disclaimer, the term of this patent is extended or adjusted under 35 U.S.C. 154(b) by 433 days.

(21) Appl. No.: 15/064,996

(22) Filed: Mar. 9, 2016

(65) Prior Publication Data

US 2016/0281199 A1    Sep. 29, 2016

Related U.S. Application Data

(60) Provisional application No. 62/131,373, filed on Mar. 11, 2015.

(51) Int. Cl.
| | | |
|---|---|---|
| *B21G 1/00* | (2006.01) | |
| *C22F 1/00* | (2006.01) | |
| *A61B 17/00* | (2006.01) | |
| *A61B 17/06* | (2006.01) | |

(52) U.S. Cl.
CPC ........ *C22F 1/006* (2013.01); *A61B 17/06066* (2013.01); *B21G 1/00* (2013.01); *A61B 2017/00526* (2013.01); *A61B 2017/00867* (2013.01); *A61B 2017/06095* (2013.01)

(58) Field of Classification Search
CPC  C22F 1/006; A61B 17/34; A61B 2017/00526
See application file for complete search history.

(56) References Cited

U.S. PATENT DOCUMENTS

| | | | | |
|---|---|---|---|---|
| 5,219,358 A | * | 6/1993 | Bendel | A61B 17/0469 606/139 |
| 5,330,441 A | * | 7/1994 | Prasad | A61B 17/06066 165/5 |
| 5,935,138 A | * | 8/1999 | McJames, II | A61B 17/06066 606/139 |
| 2002/0007209 A1 | * | 1/2002 | Scheerder | A61F 2/915 623/1.15 |
| 2010/0198256 A1 | * | 8/2010 | Loubens | A61B 17/0469 606/223 |

FOREIGN PATENT DOCUMENTS

CA         2859909 A1 *  5/2013  ......... A61B 18/1477

* cited by examiner

*Primary Examiner* — Anthony J Zimmer
(74) *Attorney, Agent, or Firm* — Young & Thompson

(57) ABSTRACT

A method for manufacturing a surgical needle produced from a wire made of a hyperelastic or superelastic alloy including a Ni—Ti alloy base includes:
  carrying out a cold shaping or a shaping at ambient temperature of the curved profile of the needle in an appropriate support;
  subjecting the needle in its support to a thermal treatment in order to memorize the imposed curved-profile geometry;
  cleaning the needle via a chemical stripping of the electrochemical or electrolytic polishing type or via a chemical solution in order to remove the layer of oxide deposited on the needle during its thermal treatment.

11 Claims, 1 Drawing Sheet

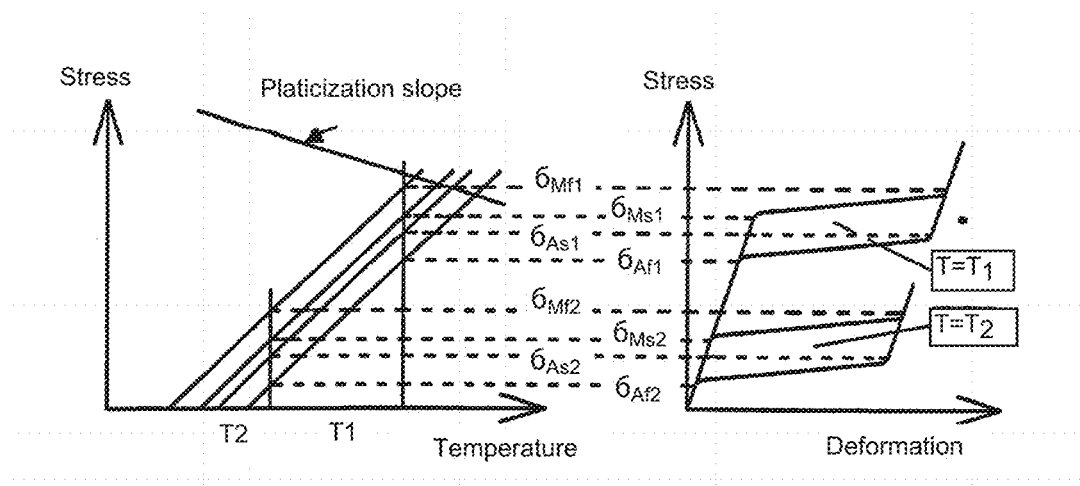

HYPERELASTIC NEEDLES

The present invention relates to improvements applied to methods for manufacturing surgical needles manufactured from hyperelastic alloys for use in celioscopic or endoscopic procedures.

From the patent EP 0529675 of Aug. 31, 1992, a surgical needle is known, which is produced from a shape memory alloy that has a first state referred to as "low-temperature" state and a second state referred to as "high-temperature" state.

In its low-temperature state, the needle can have an elongate shape in order to allow its passage into a straight tube.

In its high-temperature state, the needle assumes the shape of a predetermined arc and it is then suitable for use as a surgical needle.

The needle according to the patent EP 0529675 is particularly suitable for endoscopic procedures in which the elements are led into the surgical site passing through a cannula or a trocar having an internal diameter of small dimension.

However, the needle described in the patent EP 0529675 has disadvantages, since it is necessary to bring the body of the needle arranged in the surgical site next to a heat source so that it assumes a configuration curved according to a predetermined arc.

From the patent EP 1251785 of which the applicant is the holder, a surgical needle is known which consists of a hyperelastic alloy which, after treatment, has two distinct states making it possible, on the one hand, to force the needle into a substantially elongate position, when it is accommodated in the internal bore of a cannula or of an applicator and, on the other hand, when it is extracted from the cannula or the applicator, to be able to assume a curved profile in the shape of an arc of a circle due to its own properties of superelasticity or hyperelasticity.

The object of the invention is to improve the method for manufacturing the hyperelastic needle in order to maintain the two distinct states that make it possible for the needle to switch from an elongate shape contained in the cannula to a curved shape in the surgical site while guaranteeing that the needle has resistance to bending during the perforation of the tissues.

According to the present invention, the method for manufacturing a surgical needle produced from a wire made of a hyperelastic or hyperelastic alloy including a nickel (Ni) and titanium (Ti) base consists in:
- carrying out a cold shaping or a shaping at ambient temperature of a curved profile of the needle in an appropriate support;
- subjecting the needle in its support to a thermal treatment in order to memorize the imposed curved-profile geometry
- cleaning the needle by means of a chemical solution in order to remove the layer of oxide deposited on the needle during its thermal treatment.

In the manufacturing method according to the present invention, the needle in its support is subjected to annealing at the heating temperature of 470° C. for 15 minutes followed by cooling with ice water in order to memorize the imposed curved-profile geometry.

In the manufacturing method according to the present invention, the temperature of the ice water is between 3 and 5° C.

In the manufacturing method according to the present invention, the chemical cleaning solution consists of $HF+HNO_3+H_2O_2$ in the respective proportions of 1:3:6.

In the manufacturing method according to the present invention, the duration of the chemical attack for cleaning the needle with the solution is between 1 and 3 minutes.

In the manufacturing method according to the present invention, before the cold shaping, the needle is subjected to a thermomechanical treatment making it possible to increase its resistance to bending by increasing the difference between the temperature at the end of the austenite-martensite transformation and the temperature of use.

In the manufacturing method according to the present invention, the profile of the wire of the needle is modified so that the latter has a non-circular cross-section.

DESCRIPTION OF THE INVENTION

The method for manufacturing the surgical needle produced from a wire made of a hyperelastic or superelastic alloy including a nickel (Ni) and titanium (Ti) base includes a first step of cold shaping or shaping at ambient temperature of the curved profile of the needle in an appropriate support.

This step comprises the attachment of a wire made of a nickel (Ni) and titanium (Ti) based alloy in a specific support which makes it possible to impose (at ambient temperature) and to retain (at elevated temperatures) the shape of an arch having a radius of curvature that corresponds to the desired profile of the needle in a position of use in the surgical site.

The table below summarizes the geometry of the radius of curvature that has to be imposed on the alloy wires of the needle as a function of its diameter during the shaping step:

TABLE 1

| Diameter of the wires mm | Radius of curvature, mm | Deformation External fiber, % |
| --- | --- | --- |
| 1.0 ± 0.05 | 11.46 | 4.4 |
| 0.6 ± 0.05 | 8.28 | 3. |

The method for manufacturing the surgical needle comprises a second step which consists in subjecting the needle in its support to a thermal treatment in order to memorize the imposed geometry.

This thermal treatment makes it possible to memorize the geometry of the radius of curvature imposed during the first step of the manufacturing method. The regimen of thermal treatment (annealing) is the following: 470° C. for 15 minutes followed by cooling with ice water at a temperature of approximately 3 to 5° C.

The method for manufacturing the surgical needle comprises a third step which consists in cleaning the needle by means of a chemical stripping of the electrochemical or electrolytic polishing type or by means of a chemical solution in order to remove the layer of oxide deposited on said needle during its thermal treatment.

In the case of electrolytic polishing, it is provided to use a mixture of phosphoric acid and sulfuric acid, the concentrations of which depend on the adjustments of the current density, on the temperature of the electrolyte bath, and on the duration of the treatment.

In the case of the use of a chemical solution, the latter consists mainly of hydrofluoric acid (HF) and nitric acid ($HNO_3$) according to the following formulation:

$HF+HNO_3+H_2O_2$ in the respective proportions by volume of 1:3:6.

The duration of the chemical attack can vary between 1 and 3 minutes depending on the chemical concentrations of each component of the solution.

The manufacturing method according to the present invention was validated experimentally using the following methodology:

- for each diameter indicated in Table 1 above, the alloy wire is shaped with the different radii of curvature,
- after the thermal treatment, each sample is inserted in a catheter in an elongate or straight position and then deployed so it can assume its configuration in accordance with the predetermined radius of curvature,
- this operation was repeated five to ten times and followed by an evaluation of the restored shape.

This experimentation made it possible to verify that the storage of the needle in a catheter in elongate position does not interfere with its superelastic behavior and that no irreversible plastic deformation is generated in the needle.

According to a variant, the manufacturing method according to the present invention can comprise a step of thermomechanical treatments making it possible to improve the resistance to bending of the needles in order to guarantee stability of the position of the latter during the perforation of the tissues.

For this purpose, it is necessary, beforehand and before the cold shaping of the needle, to modify the functional properties of the shape memory materials of hyperelastic or superelastic type that include a nickel (Ni) and titanium (Ti) base by adjusting the regimens of the thermomechanical treatments.

For a given alloy, the resistance of the needles and, in particular, the resistance to bending can be increased if the difference between the temperature at the end of the martensitic transformation and the temperature of use becomes larger.

FIG. 1 shows the influence of this difference between the temperature at the end of the martensitic transformation and the temperature of use.

The manufacturing method according to the invention provides for a thermomechanical treatment of the alloy used by applying a variable stress $\delta_{Ms1}$ or $\delta_{Ms2}$ maintained at a constant temperature $T_1$ or $T_2$ in order to increase the difference between the temperature at the end of the martensitic transformation and the temperature of use (FIG. 1).

At the start, the alloy wire that forms the needle is completely austenitic and the stress is increased until the transformation zone has been passed through. The stress is then released in order to return to the initial state.

When the stress goes from 0 to $\delta_{Ms1}$ or $\delta_{Ms2}$, the relationship is linear and the behavior corresponds to that of the elastic austenite characterized by its Young's modulus.

When the stress varies between $\delta_{Ms1}$ and $\delta_{Mf1}$ or $\delta_{Ms2}$ and $\delta_{Mf2}$, one enters the transformation region where one observes an "apparent rigidity" (slope in the transformation zone) less than the Young's modulus and it is at this time that the phase transformation occurs.

Finally, when the stress becomes greater than $\delta_{Mf1}$ or $\delta_{Mf2}$, the elastic regimen of the oriented martensite is recovered. When the stress is released, the same steps re-occur in a reversed order at lower stress levels (between $\delta_{As1}$ and $\delta_{Af1}$ or $\delta_{As2}$ and $\delta_{Af2}$).

One notes that the phase transformation occurs at higher stress levels as the difference between these temperatures increases.

One notes that the superelastic curve obtained at a temperature $T_1$ corresponds to a higher stress level and thus exhibits a higher resistance than the resistance at a lower temperature $T_2$.

Precautions have to be taken in order to keep the stress induced in the material during its deformation from exceeding the starting stress of conventional plastic deformation. If the latter stress is exceeded, the plasticizing of the material will cause a definitive loss of the superelastic properties.

This increase in the difference between the temperature at the end of the martensitic transformation and the temperature of use enables an increase in the resistance to bending of the needle.

According to another variant, the manufacturing method according to the present invention can comprise a step consisting in modifying the profile of the wire of the needle, which makes it possible to improve the resistance to bending of the needles in order to guarantee stability of the position of the latter during the perforation of tissues.

In order to guarantee satisfactory operation of a suturing needle, the bending in the plane of the initial curvature must be favored in comparison to the other bending planes. This condition is found to be very important from the standpoint of the quality of the suture, since it makes it possible to guarantee the stability of the position of the needle during the perforation of the tissues, mainly when the force applied to the end of the needle does not remain exactly in the plane of its average fiber.

In order to satisfy this condition of non-deviation of the body of the needle, it is necessary to replace the circular cross-section of the latter by a non-circular cross-section having a moment of inertia relative to the axis Y perpendicular to the suture force that is less than the moment of inertia relative to the axis Z parallel to that of the force.

The larger the difference between the moments of inertia relative to the axes Y and Z is, the better the guarantee is that the bending of the needle will take place in its plane of initial curvature, even if the suturing force is slightly inclined relative to this same plane.

The selection of a non-circular cross-section thus has a clear advantage over a circular cross-section, since it becomes possible to guarantee non-deviation of the needle in the case of slight variations in its position relative to a suture point.

According to the invention, the method for manufacturing a surgical needle produced from a wire made of a hyperelastic or superelastic alloy including a nickel (Ni) and titanium (Ti) base is not limited to the applications that have just been described, and it should be understood that the preceding description was given only as an example and in no way limits the scope of the invention, which one would not exceed by replacing the described implementation details with any other equivalent.

The invention claimed is:

1. A method for manufacturing a surgical needle produced from a wire made of a hyperelastic or superelastic alloy including a nickel (Ni) and titanium (Ti) base, which method comprises:
   carrying out a shaping at a surrounding temperature of a curved profile of the needle in an appropriate support;
   subjecting the needle in the support to a thermal treatment in order to memorize the imposed curved profile geometry, by means of an annealing at a heating temperature of 470° C. for 15 minutes followed by cooling with ice water in order to memorize the imposed curved profile geometry;

cleaning the needle by means of an electrochemical chemical stripping or an electrolytic polishing or by means of a chemical solution in order to remove the layer of oxide deposited on the needle during its thermal treatment; and subjecting the needle, before the shaping, to a thermomechanical treatment to increase the needle's resistance to bending by increasing the difference between the temperature at the end of the austenite-martensite transformation and the temperature of use.

2. The method for manufacturing a surgical needle according to claim 1, wherein the temperature of the ice water is between 3 and 5° C.

3. The method for manufacturing a surgical needle according to claim 1, wherein the chemical cleaning solution consists of $HF+HNO_3+H_2O_2$ in the respective proportions by volume of 1:3:6.

4. The method for manufacturing a surgical needle according to claim 1, wherein the duration of the chemical attack for the cleaning of the needle with the solution is between 1 and 3 minutes.

5. The method for manufacturing a surgical needle according to claim 1, further comprising modifying the profile of the wire of the needle so that the latter has a non-circular cross-section.

6. The method for manufacturing a surgical needle according to claim 1,
wherein the step of cleaning the needle to remove the layer of oxide deposited on the needle during its thermal treatment is performed by means of the chemical solution, the chemical cleaning solution comprising $HF+HNO_3+H_2O_2$ in the respective proportions by volume of 1:3:6.

7. The method for manufacturing a surgical needle according to claim 6, wherein the duration of the chemical attack for the cleaning of the needle with the solution is between 1 and 3 minutes.

8. The method for manufacturing a surgical needle according to claim 6, further comprising modifying the profile of the wire of the needle so that the latter has a non-circular cross-section.

9. A method for manufacturing a surgical needle produced from a wire made of a hyperelastic or superelastic alloy including a nickel (Ni) and titanium (Ti) base, comprising the steps of:
carrying out a shaping at a surrounding temperature of a curved profile of the needle in an appropriate support;
subjecting the needle in the support to a thermal treatment in order to memorize the imposed curved profile geometry, by means of an annealing at a heating temperature of 470° C. for 15 minutes followed by cooling with ice water in order to memorize the imposed curved profile geometry; and
cleaning the needle by means of a chemical solution in order to remove the layer of oxide deposited on the needle during its thermal treatment, wherein the chemical cleaning solution consists of $HF+HNO3+H2O2$ in the respective proportions by volume of 1:3:6.

10. The method for manufacturing a surgical needle according to claim 6, wherein the duration of the chemical attack for the cleaning of the needle with the solution is between 1 and 3 minutes.

11. The method for manufacturing a surgical needle according to claim 6, further comprising modifying the profile of the wire of the needle so that the latter has a non-circular cross-section.

* * * * *